United States Patent [19]

Rivier et al.

[11] Patent Number: 4,605,642
[45] Date of Patent: Aug. 12, 1986

[54] CRF ANTAGONISTS

[75] Inventors: Catherine L. Rivier; Jean E. F. Rivier; Wylie W. Vale, Jr., all of La Jolla; Marvin R. Brown, Del Mar, all of Calif.

[73] Assignee: The Salk Institute for Biological Studies, San Diego, Calif.

[21] Appl. No.: 583,092

[22] Filed: Feb. 23, 1984

[51] Int. Cl.[4] .................. C07K 7/10; A61K 37/24
[52] U.S. Cl. ...................... 514/12; 530/324
[58] Field of Search ............... 424/177; 260/112.5 R; 514/12; 436/817

[56] References Cited

U.S. PATENT DOCUMENTS 4,415,558  11/1983  Vale et al. .................. 260/112.5 R

OTHER PUBLICATIONS

"Characterization of a 41-Residue Ovine Hypothalamic Peptide that Stimulates Secretation of Corticotropin and β-Endorphin"-Science, vol. 213, pp. 1394-1397.
Margioris et al., *Endocrinology*, 113(2), 663-671, 1983.
Rivier et al., *Science*, vol. 224, 889-891 (1984).
Gold et al., *Am. J. Psychiatry*, 619-627 (1984).
Stodman's Medical Dictionary, 23rd ed., The Williams and Wilkins Co., Baltimore, p. 1346.
Spiess et al., *Proc. Natl. Acad. Sci. USA*, vol. 78, No. 10, 1981, pp. 6517-6521.
Rivier et al., *Endocrinology*, vol. 110, No. 1, 1982, pp. 272-278.

*Primary Examiner*—Delbert R. Phillips
*Assistant Examiner*—F. T. Moezie
*Attorney, Agent, or Firm*—Fitch, Even, Tabin & Flannery

[57] ABSTRACT

Several polypeptide analogs of the known members of the corticotropin releasing factor (CRF) family have been synthesized and tested including human and rat CRF which have the formula: H-Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-$NH_2$. Peptides are herein disclosed that are potent competitive antagonists of CRF in mammals. One which has been found to be particularly potent is: H-Leu-Asp-Leu-Thr-Phe-His-Leu-Leu-Arg-Glu-Met-Leu-Glu-Met-Ala-Lys-Ala-Glu-Gln-Glu-Ala-Glu-Gln-Ala-Ala-Leu-Asn-Arg-Leu-Leu-Leu-Glu-Glu-Ala-$NH_2$. These antagonists or pharmaceutically or veterinarily acceptable salts thereof, dispersed in a pharmaceutically or veterinarily acceptable liquid or solid carrier, can be administered to mammals, including humans, to achieve a prevent elevation of ACTH, β-endorphin, β-lipotropin, other products of the pro-opiomelanocortin gene and corticosterone levels and/or a lowering of brain-mediated responses to stress over an extended period of time. They may also be used to affect mood, memory and learning, as well as diagnostically.

20 Claims, No Drawings

CRF ANTAGONISTS

This invention was made with Government support under Grants Nos. AM-26741, AM 20,917 and HD 13,527, awarded by the National Institutes of Health. The Government has certain rights in this invention.

This invention is directed to peptides and to methods for pharmaceutical treatment of mammals using such peptides. More specifically, the invention relates to antagonists of the hentetracontapeptide CRF, to pharmaceutical compositions containing CRF antagonists and to methods of treatment of mammals using CRF antagonists.

BACKGROUND OF THE INVENTION

Experimental and clinical observations have supported the concept that the hypothalamus plays a key role in the regulation of adenohypophysial corticotropic cells secretory functions. Over 25 years ago, Guillemin, Rosenberg and Saffran and Schally independently demonstrated the presence of factors in hypothalamus which would increase the rate of ACTH secretion by the pituitary gland incubated in vitro or maintained in an organ culture. None of the secretagogs characterized met the criteria expected of a physiologic corticotropin releasing factor (CRF) until ovine CRF (oCRF) was characterized in 1981 and, as disclosed in U.S. Pat. No. 4,415,558, was found to have the formula: H-Ser-Gln-Glu-Pro-Pro-Ile-Ser-Leu-Asp-Leu-Thr-Phe-His-Leu-Leu-Arg-Glu-Val-Leu-Glu-Met-Thr-Lys-Ala-Asp-Gln-Leu-Ala-Gln-Gln-Ala-His-Ser-Asn-Arg-Lys-Leu-Leu-Asp-Ile-Ala-$NH_2$.

Sauvagine is a 40-residue, amidated generally similar peptide which was isolated from the skin of the South American frog Phyllomedusa sauvagei. It was characterized by Erspamer et al. and was described in *Regulatory Peptides*, Vol. 2 (1981), pp. 1-13. Sauvagine has the formula: pGlu-Gly-Pro-Pro-Ile-Ser-Ile-Asp-Leu-Ser-Leu-Glu-Leu-Leu-Arg-Lys-Met-Ile-Glu-Ile-Glu-Lys-Gln-Glu-Lys-Glu-Lys-Gln-Gln-Ala-Ala-Asn-Asn-Arg-Leu-Leu-Leu-Asp-Thr-Ile-$NH_2$. Urotensin I is a homologous 41-residue peptide which was isolated from the urophyses of teleost fish as reported in Ichikawa, et al. *Peptides*, 3, 859 (1982). Sauvagine, Urotensin I, and members of the CRF family have been reported to have biological activity in lowering blood pressure in mammals and in stimulating the secretion of ACTH and $\beta$-endorphin.

SUMMARY OF THE INVENTION

Competitive antagonists of the 41-residue CRF family of peptides have been discovered which have the following formula: Y-$R_8$-$R_9$-leu-$R_{11}$-$R_{12}$-$R_{13}$-leu-leu-Arg-$R_{17}$-$R_{18}$-$R_{19}$-Glu-$R_{21}$-$R_{22}$-$R_{23}$-$R_{24}$-$R_{25}$-$R_{26}$-$R_{27}$-$R_{28}$-$R_{29}$-Gln-ala-$R_{32}$-$R_{33}$-Asn-Arg-$R_{36}$-$R_{37}$-$R_{38}$-$R_{39}$-$R_{40}$-$R_{41}$-$NH_2$ wherein Y is an acyl group having 7 or less carbon atoms or hydrogen; $R_8$ is ala, Gly, Gln, Ile, leu, Nle, Phe, Val or des-$R_8$; $R_9$ is Asp, Glu or des-$R_9$; $R_{12}$, $R_{19}$ and $R_{24}$ are selected from the group consisting of leu, Ile, ala, Asn, Gly, Val, Nle, Phe and Gln; $R_{11}$ is Thr or Ser; $R_{13}$ is His, Tyr or Glu; $R_{17}$ is Glu, Asn or Lys; $R_{18}$ is Val, Nle or Met; $R_{21}$ is Met, Nva, Ile, ala, leu, Nle, Val, Phe or Gln; $R_{22}$ is ala, Thr, Asp or Glu; $R_{23}$ is Arg, Orn, Har or Lys; $R_{25}$ is Asp or Glu; $R_{26}$ is Gln, Asn or Lys; $R_{27}$ is leu, Ile, ala, Val, Nva, Met, Nle, Phe, Asp, Asn, Gln or Glu; $R_{28}$ is ala, Arg or Lys; $R_{29}$ is Gln or Glu, $R_{32}$ is His, Gly, Tyr or ala; $R_{33}$ is Ser, Asn, leu, Thr or ala; $R_{36}$ is Lys, Orn, Arg, Har or leu; $R_{37}$ is leu or Tyr; $R_{38}$ is Met or leu; $R_{39}$ is Glu or Asp; $R_{40}$ is Ile, Thr, Glu, ala, Val, leu, Nle, Phe, Nva, Gly or Gln; and $R_{41}$ is ala, Ile, Gly, Val, leu, Nle, Phe, Nva or Gln; or a nontoxic addition salt thereof.

Pharmaceutical compositions in accordance with the invention include such CRF antagonists, or nontoxic addition salts thereof, dispersed in a pharmaceutically or veterinarily acceptable liquid or solid carrier. The administration of such peptides or pharmaceutically or veterinarily acceptable addition salts thereof to mammals, particularly humans, in accordance with the invention may be carried out for the regulation of secretion of ACTH, $\beta$-endorphin, $\beta$-lipotropin, other products of the pro-opiomelanocortin gene and corticosterone and/or for the lowering of stress responses and/or for affecting mood, behavioral, metabolic and gastrointestinal functions and autonomic nervous system activities. Furthermore CRF antagonists may be used for the evaluation of the status of pituitary, metabolic, cardiovascular, gastrointestinal or central nervous system functions.

DETAILED DESCRIPTION OF THE PREFERRED EMBODIMENTS

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations to identify the alpha-amino acid residues, and where the amino acid residue has isomeric forms, it is the L-form of the amino acid that is represented unless otherwise expressly indicated, e.g. Ser=L-serine, Nle=L-norleucine, Nva=norvaline, Har=homoarginine, Orn=ornithine, etc. In addition the following abbreviations are used: leu=either L-leucine or C$\alpha$CH$_3$-L-leucine (CML) and ala=either L-alanine or C$\alpha$CH$_3$-L-alanine(CMA).

The invention provides antagonists of CRF having the following Formula (I): Y-$R_8$-$R_9$-leu-$R_{11}$-$R_{12}$-$R_{13}$-leu-leu-Arg-$R_{17}$-$R_{18}$-$R_{19}$-Glu-$R_{21}$-$R_{22}$-$R_{23}$-$R_{24}$-$R_{25}$-$R_{26}$-$R_{27}$-$R_{28}$-$R_{29}$-Gln-ala-$R_{32}$-$R_{33}$-Asn-Arg-$R_{36}$-$R_{37}$-$R_{38}$-$R_{39}$-$R_{40}$-$R_{41}$-$NH_2$ wherein Y is an acyl group having 7 or less carbon atoms or hydrogen; $R_8$ is ala, Gly, Gln, Ile, leu, Nle, Phe, Val or des-$R_8$; $R_9$ is Asp, Glu or des-$R_9$; $R_{12}$, $R_{19}$ and $R_{24}$ are selected from the group consisting of leu, Ile, ala, Asn, Gly, Val, Nle, Phe and Gln; $R_{11}$ is Thr or Ser; $R_{13}$ is His, Tyr or Glu; $R_{17}$ is Glu, Asn or Lys; $R_{18}$ is Val, Nle or Met; $R_{21}$ is Met, Nva, Ile, ala, leu, Nle, Val, Phe or Gln; $R_{22}$ is ala, Thr, Asp or Glu; $R_{23}$ is Arg, Orn, Har or Lys; $R_{25}$ is Asp or Glu; $R_{26}$ is Gln, Asn or Lys; $R_{27}$ is leu, Ile, ala, Val, Nva, Met, Nle, Phe, Asp, Asn, Gln or Glu; $R_{28}$ is ala, Arg or Lys; $R_{29}$ is Gln or Glu, $R_{32}$ is His, Gly, Tyr or ala; $R_{33}$ is Ser, Asn, leu, Thr or ala; $R_{36}$ is Lys, Orn, Arg, Har or leu; $R_{37}$ is leu or Tyr; $R_{38}$ is Met or leu; $R_{39}$ is Glu or Asp; $R_{40}$ is Ile, Thr, Glu, ala, Val, leu, Nle, Phe, Nva, Gly or Gln; $R_{41}$ is ala, Ile, Gly, Val, leu, Nle, Phe, Nva or Gln; or a nontoxic addition salt thereof.

These antagonists that have been synthesized exhibit excellent binding to pituitary receptors for native CRF. These antagonists preferably include residues having a high alpha-helical forming potential as follows: $R_8$ is leu or des-$R_8$, $R_{11}$ is Thr, $R_{12}$ is Phe or leu, $R_{13}$ is His or Glu, $R_{17}$ is Glu, $R_{18}$ and $R_{21}$ are Met or Nle, $R_{19}$ and $R_{37}$ are leu, $R_{22}$ and $R_{41}$ are ala, $R_{23}$ is Lys, $R_{24}$ and $R_{28}$ are ala, $R_{25}$ and $R_{39}$ are Glu, $R_{26}$ is Gln, $R_{27}$ is Glu or leu, $R_{29}$ is Glu R$_{32}$ is His or ala, R$_{33}$ is Ser or leu, R$_{38}$ is leu and R$_{40}$ is Ile or Glu. One analog which has been found to be particularly potent is: H-Asp-Leu-Thr-Phe-His-Leu-Leu-Arg-Glu-Met-Leu-Glu-Met-Ala-Lys-Ala-Glu-Gln-Ala-Glu-Gln-Ala-Ala-Leu-Asn-Arg-Leu-Leu-Leu-Glu-Glu-Ala-NH$_2$ and is hereinafter referred to as AHC(8-41) (for alpha-helical CRF having residues 8 through 41).

The peptides are synthesized by a suitable method, such as by exclusively solid-phase techniques, by partial solid-phase techniques, by fragment condensation or by classical solution addition. Certain CRF antagonists which do not include D-isomer residues or unnatural amino acid residues may also be synthesized by recently developed recombinant DNA techniques.

Synthesis by the use of recombinant DNA techniques, for purposes of this application, should be understood to include the suitable employment of a structural gene coding for the desired form of CRF analog. The synthetic CRF peptide may be obtained by transforming a microorganism using an expression vector including a promoter and operator together with such structural gene and causing such transformed microorganism to express the CRF peptide. A non-human animal may also be used to produce the CRF peptide by gene-farming using such a structural gene and the general techniques set forth in U.S. Pat. No. 4,276,282 issued June 30, 1981 or using microinjection of embryos as described in WO83/01783 published May 26 1983 and WO82/04443 published Dec. 23, 1982. The synthetic CRF peptide is then suitably recovered from the animal by extraction from sera or the like.

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

Also considered to be within the scope of the present invention are intermediates of the Formula (II): X$^1$-R$_8$-R$_9$(X$^5$)-leu-R$_{11}$(X$^2$)-R$_{12}$(X$^4$)-R$_{13}$(X or X$^5$)-leu-leu-Arg(X$^3$)-R$_{17}$(X$^4$,X$^5$, or X$^6$)-R$_{18}$-R$_{19}$(X$^4$)-Glu(X$^5$)-R$_{21}$-R$_{22}$(X$^2$ or X$^5$)-R$_{23}$(X$^3$ or X$^6$)-R$_{24}$(X$^4$)-R$_{25}$(X$^5$)-R$_{26}$(X$^4$ or X$^6$)-R$_{27}$(X$^4$ or X$^5$)-R$_{28}$(X$^3$ or X$^6$)-R$_{29}$(X$^4$ or X$^5$)-Gln(X$^4$)-ala-R$_{32}$(X)-R$_{33}$(X$^2$ or X$^4$)-Asn(X$^4$)-Arg(X$^3$)-R$_{36}$(X$^3$ or X$^6$)-R$_{37}$(X)-R$_{38}$-R$_{39}$(X$^5$)-R$_{40}$(X$^2$ or X$^4$ or X$^5$)-R$_{41}$(X$^4$)-X$^7$ wherein: the R-groups are as hereinbefore defined.

X$^1$ is either hydrogen or an α-amino protecting group. The α-amino protecting groups contemplated by X$^1$ are those known to be useful in the art in the stepwise synthesis of polypeptides. Among the classes of α-amino protecting groups covered by X$^1$ are (1) acyl-type protecting groups, such as formyl, acrylyl(Acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenylmethyloxycarbonyl (FMOC), cyclopentyloxycarbonyl, adamantyloxycarbonyl, and cyclohexyloxycarbonyl; and (5) thiourethan-type protecting groups, such as phenylthiocarbonyl. The preferred α-amino protecting group is BOC.

X$^2$ is a protecting group for the hydroxyl group of Thr and Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl (DCB). The most preferred protecting group is Bzl. X$^2$ can be hydrogen, which means there is no protecting group on the hydroxyl group.

X$^3$ is a protecting group for the guanidino group of Arg or Har preferably selected from the class consisting of nitro, p-toluenesulfonyl(Tos), Z, adamantyloxycarbonyl and BOC, or is hydrogen. Tos is most preferred.

X$^4$ is hydrogen or a protecting group, preferably xanthyl(Xan), for the amido group of Asn or Gln.

X$^5$ is hydrogen or an ester-forming protecting group for the β- or γ-carboxyl group of Asp or Glu, preferably selected from the class consisting of benzyl, 2,6-dichlorobenzyl, methyl, ethyl and t-butyl ester. OBzl is most preferred.

X$^6$ is hydrogen or a protecting group for the side chain amino substituent of Lys or Orn. Illustrative of suitable side chain amino protecting groups are Z, 2-chlorobenzyloxycarbonyl(2-Cl-Z), Tos, t-amyloxycarbonyl(Aoc), BOC and aromatic or aliphatic urethan-type protecting groups as specified hereinbefore.

When His is present, X is hydrogen or a protecting group for the imidazole nitrogen such as Tos or 2,4-dinitrophenyl(DNP), and when Tyr is present, X is hydrogen or a protecting group for the hydroxyl group such as DCB. When Met is present, the sulfur may be protected, if desired, with oxygen.

The selection of a side chain amino protecting group is not critical except that it should must be one which is not removed during deprotection of the α-amino groups during the synthesis. Hence, the α-amino protecting group and the side chain amino protecting group cannot be the same.

X$^7$ is NH$_2$, a protecting group such as an ester or an anchoring bond used in solid phase synthesis for linking to a solid resin support, preferably one represented by the formulae:

—NH-benzhydrylamine (BHA) resin support and
—NH-paramethylbenzhydrylamine (MBHA) resin support. Cleavage from a BHA or MBHA resin directly gives the CRF analog amide. By employing a methyl-derivative of such a resin, a methyl-substituted amide can be created.

In the formula for the intermediate, at least one of X, X$^1$, X$^2$, X$^3$, X$^4$, X$^5$ and X$^6$ is a protecting group. The particular amino acid chosen for each the R-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selected for removing the α-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

For the acyl group at the N-terminal represented by Y, acetyl, formyl, acrylyl and benzoyl are preferred.

Thus, the present invention is also considered to provide a process for the manufacture of compounds defined by the Formula (I) comprising (a) forming a peptide having at least one protective group and having the Formula (II) wherein: $X, X^1, X^2, X^3, X^4, X^5$ and $X^6$ are each either hydrogen or a protective group, and $X^7$ is either a protective group or an anchoring bond to resin support or $NH_2$ and (b) splitting off the protective group or groups or anchoring bond from said peptide of the Formula (II) and (c) if desired, converting a resulting peptide into a nontoxic addition salt thereof.

When the peptides are prepared by chemical synthesis, they are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is commenced from the C-terminal end of the peptide by coupling a protected α-amino acid to a suitable resin as generally set forth in U.S. Pat. No. 4,244,946 issued Jan. 21, 1981 to Rivier et al., the disclosure of which is incorporated herein by reference. Such a starting material for an antagonist based upon human CRF can be prepared by attaching α-amino-protected Ile to a BHA resin.

Ile protected by BOC is coupled to the BHA resin using methylene chloride and dimethylformamide (DMF). Following the coupling of BOC-Ile to the resin support, the α-amino protecting group is removed, as by using trifluoroacetic acid(TFA) in methylene chloride, TFA alone or with HCl in dioxane. Preferably 50 volume % TFA in methylene chloride is used with 0–5 weight % 1,2 ethanedithiol. The deprotection is carried out at a temperature between about 0° C. and room temperature. Other standard cleaving reagents and conditions for removal of specific α-amino protecting groups may be used as described in Schroder & Lubke, "The Peptides", 1 pp 72–75 (Academic Press 1965).

After removal of the α-amino protecting group of Ile, the remaining α-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide(DCCI) and N,N'-diisopropyl carbodiimide(DICI).

The activating reagents used in the solid phase synthesis of the peptides are well known in the peptide art. Examples of suitable activating reagents are carbodiimides, such as N,N'-diisopropyl carbodiimide and N-ethyl-N'-(3-dimethylaminopropyl)carbodiimide. Other activating reagents and their use in peptide coupling are described by Schroder & Lubke, supra, in Chapter III and by Kapoor, *J. Phar. Sci.*, 59, pp 1–27 (1970).

Each protected amino acid or amino acid sequence is introduced into the solid phase reactor in about a fourfold excess, and the coupling is carried out in a medium of dimethylformamide(DMF):CH$_2$Cl$_2$ (1:1) or in DMF or CH$_2$Cl$_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the α-amino protecting group prior to the coupling of the next amino acid. The coupling reactions can be performed automatically, as on a Beckman 990 automatic synthesizer, using a program such as that reported in Rivier et al., *Biopolymers*, 1978, 17, pp. 1927–1938.

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2, X^3, X^4, X^5$ and $X^6$ and the α-amino protecting group $X^1$ (unless it is an acyl group which is intended to be present in the final peptide), to obtain the peptide. When using hydrogen fluoride for cleaving, anisole or cresole and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate S-alkylation.

The following Example sets forth the preferred method for synthesizing CRF antagonists by the solid-phase technique.

EXAMPLE 1

The synthesis of the human CRF (9-41) having the formula: H-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH$_2$ is conducted in a stepwise manner on a MBHA hydrochloride resin, such as available from Bachem, Inc., having a substitution range of about 0.1 to 0.7 mmoles/gm. resin. The synthesis is performed on an automatic Beckman 990B peptide synthesizer using a suitable program, preferably as follows:

| STEP | REAGENTS AND OPERATIONS | MIX TIMES MIN. |
|---|---|---|
| 1 | CH$_2$Cl$_2$ wash-80 ml. (2 times) | 3 |
| 2 | Methanol(MeOH) wash-30 ml. (2 times) | 3 |
| 3 | CH$_2$Cl$_2$ wash-80 ml. (3 times) | 3 |
| 4 | 50 percent TFA plus 5 percent 1,2-ethanedithiol in CH$_2$Cl$_2$—70 ml. (2 times) | 12 |
| 5 | Isopropanol wash-80 ml. (2 times) | 3 |
| 6 | TEA 12.5 percent in CH$_2$Cl$_2$—70 ml. (2 times) | 5 |
| 7 | MeOH wash-40 ml. (2 times) | 2 |
| 8 | CH$_2$Cl$_2$ wash-80 ml. (3 times) | 3 |
| 9 | Boc-amino acid (10 mmoles) in 30 ml. of either DMF or CH$_2$Cl$_2$, depending upon the solubility of the particular protected amino acid, (1 time) plus DCCI (10 mmoles) in CH$_2$Cl$_2$ | 30–300 |

Coupling of BOC-Ile results in the substitution of about 0.35 mmol. Ile per gram of resin. All solvents that are used are carefully degassed, preferably by sparging with an inert gas, e.g. helium or nitrogen, to insure the absence of oxygen that might undesirably oxidize the sulfur of the Met residue.

After deprotection and neutralization, the peptide chain is built step-by-step on the resin. Generally, one to two mmol. of BOC-protected amino acid in methylene chloride is used per gram of resin, plus one equivalent of 2 molar DCCI in methylene chloride, for two hours. When BOC-Arg(Tos) is being coupled, a mixture of 50% DMF and methylene chloride is used. Bzl is used as the hydroxyl side-chain protecting group for Ser and Thr. P-nitrophenyl ester(ONp) is used to activate the carboxyl end of Asn or Gln, and for example, BOC-Asn(ONp) is coupled overnight using one equivalent of HOBt in a 50% mixture of DMF and methylene chloride. The amido group of Asn or Gln is protected by Xan when DCCI coupling is used instead of the active ester method. 2-Cl-Z is used as the protecting group for the Lys side chain. Tos is used to protect the guanidino group of Arg and the imidazole group of His, and the side chain carboxyl group of Glu or Asp is protected by OBzl. At the end of the synthesis, the following composition is obtained BOC-Asp(OBzl)-Leu-Thr(Bzl)-Phe-His(Tos)-Leu-Leu-Arg(Tos)-Glu(OBzl)-Val-Leu-Glu(OBzl)-Met-Ala-Arg(Tos)-Ala-Glu(OBzl)-Gln(Xan)-Leu-Ala-Gln(Xan)-Gln(Xan)-Ala-His(Tos)-Ser(Bzl)-Asn(Xan)-Arg(Tos)-Lys(2-Cl-Z)-Leu-Met-Glu(OBzl)-Ile-Ile-resin support. Xan may have been partially or totally removed by TFA treatment used to deblock the α-amino protecting group.

In order to cleave and deprotect the resulting protected peptide-resin, it is treated with 1.5 ml. anisole, 0.5 ml. of methylethylsulfide and 15 ml. hydrogen fluoride (HF) per gram of peptide-resin, first at −20° C. for 20 min. and then at 0.° C. for one-half hour. After elimination of the HF under high vacuum, the resin-peptide is washed alternately with dry diethyl ether and chloroform, and the peptides are then extracted with degassed 2N aqueous acetic acid and separated from the resin by filtration.

The peptide is purified by gel permeation followed by semi-preparative HPLC as described in Rivier et al., *Peptides: Structure and Biological Function* (1979) pp. 125–128, and Rivier et al. *J. Chromatography* (1983). The chromatographic fractions are carefully monitored by HPLC, and only the fractions showing substantial purity were pooled.

EXAMPLE II

The synthetic peptide AHC(9-41) having the formula: H-Asp-Leu-Thr-Phe-His-Leu-Leu-Arg-Glu-Met-Leu-Glu-Met-Ala-Lys-Ala-Glu-Gln-Glu-Ala-Glu-Gln-Ala-Ala-Leu-Asn-Arg-Leu-Leu-Leu-Glu-Glu-Ala-NH$_2$ is synthesized generally in accordance with the procedure set forth in Example I.

Specific optical rotation of the hCRF peptide, which was synthesized and purified in the foregoing manner, was measured on a Perkin Elmer Model 141 as $[\alpha]_D^{22°} = -59.5° \pm 1.0$ (c=1 in 1% acetic acid) (with correction for the presence of H$_2$O and TFA) and had a purity of about 95%. To check whether the precise sequence was achieved, the CRF peptide was hydrolyzed in sealed evacuated tubes containing constant boiling HCl, 3 ul of thioglycol/ml. and 1 nmol of Nle (as an internal standard) for 9 hours at 140° C. Amino acid analyses of the hydrolysates using a Beckman 121 MB amino acid analyzer showed the following amino acid ratios: Asx(1.9), Thr(0.8), Glx(9.1), Ala(5.8), Met(1.9), Leu(8.0), Phe(0.9), Lys(1.0), His(1.1) and Arg(2.0), which confirmed that the 33-residue peptide structure had been obtained.

EXAMPLE III

The synthetic CRF antagonists from Examples I and II were examined for their effects on the secretion of ACTH and β-endorphin in vitro and the synthetic AHC peptide is also examined in vivo. The effectiveness of synthetic CRF antagonists to block the secretion of ACTH and β-endorphin by cultured rat pituitary cells is measured using the procedure as generally set forth in Vale et al., *Endocrinology*, 91, 562 (1972). In vivo testing is carried out using the general procedure set forth in C. Rivier et al., *Science*, 218, 377 (1982).

Based upon five independent experiments what we herein term the standard antagonist, AHC (9-41), blocks the secretion of ACTH due to 1 nMoCRF by 50%, at a concentration of 197±72 nM. The specificity of this inhibition is demonstrated by the finding of no effect of the standard antagonist on the GRF-stimulated secretion of GH, the GnRH-stimulated secretion of LH and FSH or the TRF-stimulated secretion of TSH and prolactin. The effects of the antagonist on a number of different concentrations of oCRF and the ability of several different concentrations of AHC (9-41) to inhibit ACTH secretion stimulated by a constant dose of oCRF (1 nM) are considered to demonstrate competitive inhibition.

The in vivo effect of CRF antagonists is tested on the spontaneous ACTH release by adrenalectomized rats. The iv injection of 3 mg/kg BW (2.7 nmole) causes a marked decrease in plasma ACTH levels (measured as described in Vale et al. *Science*, 213, 1394, 1981), which is statistically significant for 2 hours. In the intact, non-anesthetized rats, the antagonist induces a dose-related inhibition of CRF-induced ACTH secretion, which is significant at the 0.09 μmole dose level. The antagonist AHC (9-41) also prevents most, but not all, of the ACTH rise due to ether-exposure.

These results indicate that administration of CRF antagonists reduces the spontaneous ACTH release observed after removal of the corticosteroid feedback, totally blocks the ACTH secretion caused by CRF, and inhibits most of the stressor-induced ACTH release in intact rats. Such data are comparable to those previously obtained in our laboratory with an antiserum to CRF which demonstrate the role played by endogenous CRF in regulating ACTH secretion, Rivier, C. et al., *Science*, 218, 377-9(1982).

These results confirm the hypothesis that CRF is indeed a critical element in the regulation of ACTH under several circumstances. In addition, that CRF antagonists can partially block the ether-exposure-induced activation of the sympathetic nervous system suggest a much broader role for this neuropeptide in mediating the response to stressful stimuli.

Synthetic hCRF has been shown to be a powerful stimulator of ACTH and β-END-LI secretion in vivo in several rat preparations. Plasma levels of ACTH and β-END-LI are elevated for at least 5–20 minutes following the intraveneous administration of hCRF to nembutal-anesthesized male rats and to quiescent male or female rats with indwelling intravenous cannulae. In addition, hCRF is found to have a dramatic effect to lower blood pressure in rats and dogs.

EXAMPLE IV

The peptide hCRF(8-41) having the formula: H-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala- His-Ser-Asn-Arg-Lys-Leu-Met-Glu-Ile-Ile-NH₂ is synthesized. Testing in accordance with the general procedure set forth in Example III shows that it likewise inhibits the secretion of ACTH and β-END-LI.

EXAMPLE V

The peptide hCRF(10-41) having the formula: H-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH₂ is synthesized. Testing in accordance with the general procedure set forth in Example III shows that it likewise inhibits the secretion of ACTH and β-END-LI.

EXAMPLE VI

The peptide Carp Urotensin I(9-41) having the formula: H-Asp-Leu-Thr-Phe-His-Leu-Leu-Arg-Asn-Met-Ile-Glu-Met-Ala-Arg-Asn-Glu-Asn-Gln-Arg-Glu-Gln-Ala-Gly-Leu-Asn-Arg-Lys-Tyr-Leu-Asp-Glu-Val-NH₂ is synthesized. Testing in accordance with the general procedure set forth in Example III shows that it likewise inhibits the secretion of ACTH and β-END-LI.

EXAMPLE VII

The peptide [Ala¹⁹, Thr²²]-hCRF(9-41) having the formula: H-Asp-Leu-Thr-Phe-His-Leu-Leu-Arg-Glu-Val-Ala-Glu-Met-Thr-Arg-Ala-Glu-Gln-Leu-Ala-Gln-Gln-Ala-His-Ser-Asn-Arg-Lys-Leu-Met-Glu-Ile-Ile-NH₂ is synthesized. Testing in accordance with the general procedure set forth in Example III shows that it likewise inhibits the secretion of ACTH and β-END-LI.

EXAMPLE VIII

The peptide Carp Urotensin I(8-41) having the formula: H-Ile-Asp-Leu-Thr-Phe-His-Leu-Leu-Arg-Asn-Met-Ile-Glu-Met-Ala-Arg-Asn-Glu-Asn-Gln-Arg-Glu-Gln-Ala-Gly-Leu-Asn-Arg-Lys-Tyr-Leu-Asp-Glu-Val-NH₂ is synthesized. Testing in accordance with the general procedure set forth in Example III shows that it likewise inhibits the secretion of ACTH and β-END-LI.

EXAMPLE IX

The peptide [Glu¹³, Val²¹]-hCRF(9-41) having the formula: H-Asp-Leu-Thr-Phe-Glu-Leu-Leu-Arg-Glu-Val-Leu-Glu-Val-Ala-Arg-Ala-Glu-Gln-Leu-Ala-Gln-Gln-Ala-His-Ser-Asn-Arg-Lys-Leu-Met-Glu-Ile-Ile-NH₂ is synthesized. Testing in accordance with the general procedure set forth in Example III shows that it likewise inhibits the secretion of ACTH and β-END-LI.

EXAMPLE X

The peptide [Nle⁸, Ser¹¹, Leu³³]-hCRF(8-41) having the formula: H-Nle-Asp-Leu-Ser-Phe-His-Leu-Leu-Arg-Glu-Val-Leu-Glu-Met-Ala-Arg-Ala-Glu-Gln-Leu-Ala-Gln-Gln-Ala-His-Leu-Asn-Arg-Lys-Leu-Met-Glu-Ile-Ile-NH₂ is synthesized. Testing in accordance with the general procedure set forth in Example III shows that it likewise inhibits the secretion of ACTH and β-END-LI.

EXAMPLE XI

The peptide [Ala²¹, Leu³⁸, Nle⁴¹]-hCRF(9-41) having the formula: H-Asp-Leu-Thr-Phe-His-Leu-Leu-Arg-Glu-Val-Leu-Glu-Ala-Ala-Arg-Ala-Glu-Gln-Leu-Ala-Gln-Gln-Ala-His-Ser-Asn-Arg-Lys-Leu-Leu-Glu-Ile-Nle-NH₂ is synthesized. Testing in accordance with the general procedure set forth in Example III shows that it likewise inhibits the secretion of ACTH and β-END-LI.

EXAMPLE XII

The peptide [Nle¹²]-hCRF(10-41) having the formula: H-Leu-Thr-Nle-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH₂ is synthesized. Testing in accordance with the general procedure set forth in Example III shows that it likewise inhibits the secretion of ACTH and β-END-LI.

EXAMPLE XIII

The peptide [Acetyl-Asp⁹, Asp³⁹]-hCRF(9-41) having the formula: Ac-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Asp-Ile-Ile-NH₂ is synthesized. Testing in accordance with the general procedure set forth in Example III shows that it likewise inhibits the secretion of ACTH and β-END-LI.

EXAMPLE XIV

The peptide [Lys²³, Leu³⁸]-hCRF(8-41) having the formula: H-Leu-Asp-Leu-Thr-Phe-His-Leu-Leu-Arg-Glu-Val-Leu-Glu-Met-Ala-Lys-Ala-Glu-Gln-Leu-Ala-Gln-Gln-Ala-His-Ser-Asn-Arg-Lys-Leu-Leu-Glu-Ile-Ile-NH₂ is synthesized. Testing in accordance with the general procedure set forth in Example III shows that it likewise inhibits the secretion of ACTH and β-END-LI.

EXAMPLE XV

The peptide [Nle²¹, Tyr³²]-hCRF(9-41) having the formula: H-Asp-Leu-Thr-Phe-His-Leu-Leu-Arg-Glu-Val-Leu-Glu-Nle-Ala-Arg-Ala-Glu-Gln-Leu-Ala-Gln-Gln-Ala-Tyr-Ser-Asn-Arg-Lys-Leu-Met-Glu-Ile-Ile-NH₂ is synthesized. Testing in accordance with the general procedure set forth in Example III shows that it likewise inhibits the secretion of ACTH and β-END-LI.

EXAMPLE XVI

The peptide [Ala²¹, Met³⁷]-sauvagine(8-40) having the formula: H-Asp-Leu-Ser-Leu-Glu-Leu-Leu-Arg-Lys-Met-Ile-Glu-Ile-Ala-Lys-Gln-Glu-Lys-Glu-Lys-Gln-Gln-Ala-Ala-Asn-Asn-Arg-Leu-Leu-Met-Asp-Thr-Ile-NH₂ is synthesized. Testing in accordance with the general Procedure set forth in Example III shows that it likewise inhibits the secretion of ACTH and β-END-LI.

EXAMPLE XVII

The peptide [Ala²¹, Arg²², Ile³⁹,⁴⁰]-sauvagine(9-40) having the formula: H-Leu-Ser-Leu-Glu-Leu-Leu-Arg-Lys-Met-Ile-Glu-Ala-Arg-Lys-Gln-Glu-Lys-Glu-Lys-Gln-Gln-Ala-Ala-Asn-Asn-Arg-Leu-Leu-Leu-Asp-Ile-Ile-NH₂ is synthesized. Testing in accordance with the general procedure set forth in Example III shows that it likewise inhibits the secretion of ACTH and β-END-LI.

EXAMPLE XVIII

The peptide [Leu²⁶, Met³⁷]-sauvagine(8-40) having the formula: H-Asp-Leu-Ser-Leu-Glu-Leu-Leu-Arg- Lys-Met-Ile-Glu-Ile-Glu-Lys-Gln-Glu-Lys-Leu-Lys-Gln-Gln-Ala-Ala-Asn-Asn-Arg-Leu-Leu-Met-Asp-Thr-Ile-NH$_2$ is synthesized. Testing in accordance with the general procedure set forth in Example III shows that it likewise inhibits the secretion of ACTH and β-END-LI.

EXAMPLE XIX

The peptide [CML$^{10,15,27,37}$, CMA$^{22,32,41}$]AHC(9-41) having the formula: H-Asp-CML-Thr-Leu-Glu-CML-CML-Arg-Glu-Met-CML-Glu-Met-CMA-Lys-Ala-Glu-Gln-CML-Ala-Glu-Gln-Ala-CMA-CML-Asn-Arg-Leu-CML-Leu-Glu-Glu-CMA-NH$_2$. Testing in accordance with the general procedure set forth in Example III shows that it likewise inhibits the secretion of ACTH and β-END-LI.

EXAMPLE XX

The peptide [Nle$^{18,21}$]-AHC(9-41) having the formula: H-Asp-Leu-Thr-Phe-His-Leu-Leu-Arg-Glu-Nle-Leu-Glu-Nle-Ala-Lys-Ala-Glu-Gln-Glu-Ala-Glu-Gln-Ala-Ala-Leu-Asn-Arg-Leu-Leu-Leu-Glu-Glu-Ala-NH$_2$ is synthesized. Testing in accordance with the general procedure set forth in Example III shows that it likewise inhibits the secretion of ACTH and β-END-LI.

EXAMPLE XXI

The peptide [Nle$^{18,21}$]-AHC(9-41) having the formula: H-Asp-Leu-Thr-Phe-His-Leu-Leu-Arg-Glu-Nle-Leu-Glu-Nle-Ala-Lys-Ala-Glu-Gln-Glu-Ala-Glu-Gln-Ala-Ala-Leu-Asn-Arg-Leu-Leu-Leu-Glu-Glu-Ala-NH$_2$ is synthesized. Testing in accordance with the general procedure set forth in Example 111 shows that it likewise inhibits the secretion of ACTH and β-END-LI.

EXAMPLE XXII

The peptide [Nle$^{18,21}$]-AHC(8-41) having the formula: H-Leu-Asp-Leu-Thr-Phe-His-Leu-Leu-Arg-Glu-Nle-Leu-Glu-Nle-Ala-Lys-Ala-Glu-Gln-Glu-Ala-Glu-Gln-Ala-Ala-Leu-Asn-Arg-Leu-Leu-Leu-Glu-Glu-Ala-NH$_2$ is synthesized. Testing in accordance with the general procedure set forth in Example III shows that it likewise inhibits the secretion of ACTH and β-END-LI.

EXAMPLE XXIII

The peptide [Glu$^{13,22}$, Leu$^{12}$, Lys$^{26}$]-AHC(8-41) having the formula: H-Leu-Asp-Leu-Thr-Leu-Glu-Leu-Leu-Arg-Glu-Met-Leu-Glu-Met-Glu-Lys-Ala-Glu-Lys-Glu-Ala-Glu-Gln-Ala-Ala-Leu-Asn-Arg-Leu-Leu-Leu-Glu-Glu-Ala-NH$_2$. Testing in accordance with the general procedure set forth in Example III shows that it likewise inhibits the secretion of ACTH and β-END-LI.

EXAMPLE XXIV

The synthetic peptide [Ala$^{13}$]-AHC(9-41) having the formula: H-Asp-Leu-Thr-Phe-Ala-Leu-Leu-Arg-Glu-Met-Leu-Glu-Met-Ala-Lys-Ala-Glu-Gln-Glu-Ala-Glu-Gln-Ala-Ala-Leu-Asn-Arg-Leu-Leu-Leu-Glu-Glu-Ala-NH$_2$ is synthesized. Testing in accordance with the general procedure set forth in Example III shows that it likewise inhibits the secretion of ACTH and β-END-LI.

EXAMPLE XXV

The peptide [Leu$^{12}$, Glu$^{13}$]-AHC(9-41) having the formula: H-Asp-Leu-Thr-Leu-Glu-Leu-Leu-Arg-Glu-Met-Leu-Glu-Met-Ala-Lys-Ala-Glu-Gln-Glu-Ala-Glu-Gln-Ala-Ala-Leu-Asn-Arg-Leu-Leu-Leu-Glu-Glu-Ala-NH$_2$. Testing in accordance with the general procedure set forth in Example III shows that it likewise inhibits the secretion of ACTH and β-END-LI.

EXAMPLE XXVI

The peptide [CML$^{10,14,19,27,33,38}$]-AHC(9-41) having the formula: H-Asp-CML-Thr-Leu-Glu-CML-Leu-Arg-Glu-Met-CML-Glu-Met-Ala-Lys-Ala-Glu-Gln-CML-Ala-Glu-Gln-Ala-Ala-CML-Asn-Arg-Leu-CML-Leu-Glu-Glu-Ala-NH$_2$. Testing in accordance with the general procedure set forth in Example III shows that it likewise inhibits the secretion of ACTH and β-END-LI and causes a very significant lowering of blood pressure.

EXAMPLE XXVII

The peptide [Nle$^{18,21}$]-AHC(10-41) having the formula: H-Leu-Thr-Phe-His-Leu-Leu-Arg-Glu-Nle-Leu-Glu-Nle-Ala-Lys-Ala-Glu-Gln-Glu-Ala-Glu-Gln-Ala-Ala-Leu-Asn-Arg-Leu-Leu-Leu-Glu-Glu-Ala-NH$_2$ is synthesized. Testing in accordance with the general procedure set forth in Example III shows that it likewise inhibits the secretion of ACTH and β-END-LI.

CRF profoundly stimulates the pituitary-adrenalcortical axis, and CRF antagonists should be useful to inhibit the functions of this axis in some types of patients with high ACTH and endogenous glucocorticoid production. For example, CRF antagonists may be useful in regulating pituitary-adrenal function in patients having pituitary Cushings disease or any CRF-sensitive tumor.

Most other regulatory peptides have been found to have effects upon the endrocrine system, the central nervous system and upon the gastrointestinal tract. Because ACTH and β-END secretion is the "sine qua non" of mammal's response to stress, it was not surprising that CRF has significant effects on the brain as a mediator of many of the body's stress responses. Accordingly, CRF antagonists delivered to the brain should also find application in modifying the mood, learning and behavior of normal and mentally disordered individuals. Furthermore, CRF antagonists in the brain could ameliorate stress-induced conditions to which endogenous CRF might contribute, including some types of hypertension, infertility, decreased libido, impotentcy and hyperglycemia. Because peripherally administered CRF antagonists reduce the levels of ACTH, β-END, β-lipotropin, other pro-opiomelanocortin gene products and corticosterone, administration of the antagonists may be used to reduce the effects of all of these substances on the brain to thereby influence memory, mood, pain appreciation, etc., and more specifically, alertness, depression and/or anxiety, as well as to modulate the immune system, gastrointestinal tract and adrenalcortical growth and function.

All CRF related peptides have been shown to dialate the mesenteric vascular bed. CRF antagonists may also be of use for decreasing blood flow to the gastrointestinal tract of mammals, particularly humans. Also, oCRF influences gastric acid production, and CRF antagonists are expected to also be effective to modulate gastrointestinal functions.

CRF antagonists or the nontoxic addition salts thereof, combined with a pharmaceutically or veterinarily acceptable carrier to form a pharmaceutical composition, may be administered to mammals, including humans, either intravenously, subcutaneously, intramuscularly, percutaneously, e.g. intranasally, intracerebroventricularly or orally. The peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans may be employed by a physician to inhibit endogenous gluco-corticoid production or for possible uses outlined above. The required dosage will vary with the particular condition being treated, with the severity of the condition and with the duration of desired treatment. In order to block the stress-related effects of endogenous CRF within the central nervous system, it may be necessary to deliver the CRF antagonists into the cerebral ventricle or spinal fluid. Alternatively, a means of modifying the antagonists so that they could penetrate the blood-brain barrier should be found.

These peptides may also be used to evaluate hypothalamic pituitary adrenal function in mammals with suspected endocrine or central nervous system pathology by suitable administration followed by monitoring body functions. For example, administration may be used as a diagnostic tool to evaluate the basis of Cushings disease.

Such peptides are often administered in the form of pharmaceutically or veterinarily acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically or veterinarily-acceptable carrier. Usually, the dosage will be from about 0.01 to about 10 milligrams of the peptide per kilogram of the body weight of the host animal. As used herein all temperatures are ° C. and all ratios are by volume. Percentages of liquid materials are also by volume.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at other positions in the CRF peptide chain can be made in accordance with present or future developments without detracting from the potency of the antagonists. For instance, instead of the simple amide at the C-terminal, a lower alkyl-substituted amide, e.g. C 1-4, i.e. methylamide, ethylamide, etc, may be incorporated. Such peptides are considered as being within the scope of the invention.

Various features of the invention are emphasized in the claims which follow.

What is claimed is:

1. A composition for lowering stressinduced secretion of ACTH, $\beta$-endorphin, $\beta$-lipotropin and proopiomelanocortin-related peptides in mammals comprising an effective amount of a synthetic peptide or a nontoxic addition salt thereof having the sequence: $R_8$-$R_9$-leu-$R_{11}$-$R_{12}$-$R_{13}$-leu-leu-Arg-$R_{17}$-$R_{18}$-$R_{19}$-Glu-$R_{21}$-$R_{22}$-$R_{23}$-$R_{24}$-$R_{25}$-$R_{26}$-$R_{27}$-$R_{28}$-$R_{29}$-Gln-ala-$R_{32}$-$R_{33}$-Asn-Arg-$R_{36}$-$R_{37}$-$R_{38}$-$R_{39}$-$R_{40}R_{41}$ wherein $R_8$ is ala, Gly, Gln, Ile, leu, Nle, Phe, Val or des-$R_8$; $R_9$ is Asp, Glu or des-$R_9$; $R_{12}$, $R_{19}$ and $R_{24}$ are selected from the group consisting of leu, Ile, ala, Asn, Gly, Val, Nle, Phe and Gln; $R_{11}$ is Thr or Ser; $R_{13}$ is His, Tyr or Glu; $R_{17}$ is Glu, Asn or Lys; $R_{18}$ is Val, Nle or Met; $R_{21}$ is Met, Nva, Ile, ala, leu, Gly, Nle, Val, Phe or Gln; $R_{22}$ is ala or Thr or Glu; $R_{23}$ is Arg, Orn, and Har or Lys; $R_{25}$ is Asp or Glu; $R_{26}$ is Gln, Asn or Lys; $R_{27}$ is leu, Ile, ala, Val, Nva, Met, Nle, Phe, Asp, Asn, Gln or Glu; $R_{28}$ is ala, Arg or Lys; $R_{29}$ is Gln or Glu, $R_{32}$ is His, Gly, Tyr or ala; $R_{33}$ is Ser, Asn, leu, Thr or ala; $R_{36}$ is Lys, Orn, Arg, Har or leu; $R_{37}$ is leu or Tyr; $R_{38}$ is Met or leu; $R_{39}$ is Glu or Asp; $R_{40}$ is Ile, Thr, Glu, ala, Val, leu, Nle, Phe, Nva, Gly or Gln; and $R_{41}$ is ala, Ile, Gly, Val, leu, Nle, Phe, Nva or Gln; ala representing either L-Ala or $C\alpha CH_3$-L-Ala and leu representing either L-Leu or $C\alpha CH_3$-L-Leu; and a pharmaceutically or veterinarily acceptable liquid or solid carrier therefor.

2. A method for lowering stress-induced secretion of ACTH, $\beta$-endorphin, $\beta$-lipotropin and proopiomelanocortin-related peptides in a mammal, which method comprises intraveneously, subcutaneously, intramuscularly, percutaneously, intracerebroventricularly or orally administering to said mammal an effective amount of a composition of claim 1.

3. A method according to claim 2 which method comprises administering said effective amount intraveneously.

4. A peptide having the formula: Y-$R_8$-$R_9$-leu-$R_{11}$-$R_{12}$-$R_{13}$-leu-leu-Arg-$R_{17}$-$R_{18}$-$R_{19}$-Glu-$R_{21}$-$R_{22}$-$R_{23}$-$R_{24}$-$R_{25}$-$R_{26}$-$R_{27}$-$R_{28}$-$R_{29}$-Gln-ala-$R_{32}$-$R_{33}$-Asn-Arg-$R_{36}$-$R_{37}$-$R_{38}$-$R_{39}$-$R_{40}$-$R_{41}$-$NH_2$ wherein Y is acetyl, formyl, acrylyl, benzoyl or hydrogen; $R_8$ is ala, Gly, Gln, Ile, leu, Nle, Phe, Val or des-$R_8$; $R_9$ is Asp, Glu or des-$R_9$; $R_{12}$, $R_{19}$ and $R_{24}$ are selected from the group consisting of leu, Ile, ala, Asn, Gly, Val, Nle, Phe and Gln; $R_{11}$ is Thr or Ser; $R_{13}$ is His, Tyr or Glu; $R_{17}$ is Glu, Asn or Lys; $R_{18}$ is Val, Nle or Met; $R_{21}$ is Met, Nva, Ile, ala, leu, Gly, Nle, Val, Phe or Gln; $R_{22}$ is ala or Thr or Glu; $R_{23}$ is Arg, Orn, Har or Lys; $R_{25}$ is Asp or Glu; $R_{26}$ is Gln, Asn or Lys; $R_{27}$ is leu, Ile, ala, Val, Nva, Met, Nle, Phe, Asp, Asn, Gln or Glu; $R_{28}$ is ala, Arg or Lys; $R_{29}$ is Gln or Glu, $R_{32}$ is His, Gly, Tyr or ala; $R_{33}$ is Ser, Asn, leu, Thr or ala; $R_{36}$ is Lys, Orn, Arg, Har or leu; $R_{37}$ is leu or Tyr; $R_{38}$ is Met or leu; $R_{39}$ is Glu or Asp; $R_{40}$ is Ile, Thr, Glu, ala, Val, leu, Nle, Phe, Nva, Gly or Gln; and $R_{41}$ is ala, Ile, Gly, Val, leu, Nle, Phe, Nva or Gln; or a non toxic addition salt thereof.

5. The compound of claim 4 wherein $R_{13}$ is His, $R_{17}$ is Glu, $R_{18}$ is Val, $R_{26}$ is Gln, $R_{28}$ is Ala and $R_{36}$ is Lys.

6. The compound of claim 5 wherein $R_{21}$ is Met.

7. The compound of claim 6 wherein $R_{22}$ is Ala, $R_{23}$ is Arg, $R_{25}$ is Glu, $R_{32}$ is His, $R_{33}$ is Ser, $R_{38}$ is Met and $R_{40}$ is Ile.

8. The compound of claim 7 wherein $R_8$ is Leu, $R_{12}$ is Phe, $R_{19}$ is Leu, $R_{24}$ is Ala, $R_{27}$ is Leu and $R_{39}$ is Glu.

9. The compound of claim 7 wherein $R_8$ is Leu, $R_{12}$ is Phe, $R_{19}$ is Leu, $R_{24}$ is Ala, $R_{27}$ is Leu and $R_{41}$ is Ile.

10. The compound of claim 9 wherein Y is acetyl.

11. The compound of claim 4 wherein $R_{17}$ is Glu, $R_{19}$ and $R_{37}$ are Leu, $R_{24}$ and $R_{28}$ are Ala, and $R_{25}$ and $R_{39}$ are Glu.

12. The Compound of claim 11 wherein $R_{12}$ is Phe or Leu, $R_{13}$ is His or Glu $R_{27}$ is Glu or Leu, $R_{32}$ is His or Ala, $R_{33}$ is Ser or Leu, and $R_{40}$ is Ile or Glu.

13. The compound of claim 12 wherein $R_{18}$ is Met, $R_{22}$ and are Ala, $R_{23}$ is Lys, $R_{26}$ is Gln, $R_{29}$ is Glu and $R_{38}$ is Leu.

14. The compound of claim 13 wherein $R_8$ is Leu, $R_9$ is Asp and $R_{11}$ is Thr.

15. The compound of claim 14 wherein $R_{12}$ is Phe, $R_{13}$ is His, $R_{27}$ is Glu, $R_{32}$ is Ala, $R_{33}$ is Leu and $R_{40}$ is Glu.

16. The compound of claim 15 wherein $R_{21}$ is Met.

17. The compound of claim 4 having the formula: H-Asp-Leu-Thr-Phe-His-Leu-Leu-Arg-Glu-Met-Leu-Glu-Met-Ala-Lys-Ala-Glu-Gln-Glu-Ala-Glu-Gln-Ala-Ala-Leu-Asn-Arg-Leu-Leu-Leu-Glu-Glu-Ala-NH$_2$.

18. The compound of claim 4 having the formula: H-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH$_2$.

19. A method of inhibiting the secretion in mammals of ACTH and corticosteroids or the secretion of β-endorphin, and other pro-opiomelanocortin gene products which method comprises intraveneously, subcutaneously, intramuscularly, percutaneously, intracerebroventricularly or orally administering an effective amount between about 0.01 and about 10 milligrams, per kilogram of body weight, of the compound of claim 4.

20. A peptide having the formula: H-$R_8$-Asp-Leu-Thr-Phe-His-Leu-Leu-Arg-Glu-$R_{18}$-Leu-Glu-$R_{21}$-Ala-$R_{23}$-Ala-Glu-Gln-$R_{27}$-Ala-$R_{29}$-Gln-Ala-$R_{32}$-$R_{33}$-Asn-Arg-$R_{36}$-Leu-$R_{38}$-Glu-$R_{40}$-$R_{41}$-NH$_2$ wherein Y is acetyl, formyl, acrylyl, benzoyl or hyrdrogen; $R_8$ is Leu or des-$R_8$; $R_{18}$ is Val, Nle or Met; $R_{21}$ is Met or Nle; $R_{23}$ is Arg or Lys; $R_{27}$ is Leu or Glu; $R_{29}$ is Gln or Glu; $R_{32}$ is His or Ala; $R_{33}$ is Ser or Leu; $R_{36}$ is Lys or Leu; $R_{38}$ is Met or Leu; $R_{40}$ is Ile or Glu; and $R_{41}$ is Ala or Ile; or a nontoxic addition salt thereof.

* * * * *

UNITED STATES PATENT AND TRADEMARK OFFICE
CERTIFICATE OF CORRECTION

PATENT NO. : 4,605,642
DATED : August 12, 1986
INVENTOR(S) : Catherine L. Rivier, et al.

It is certified that error appears in the above-identified patent and that said Letters Patent is hereby corrected as shown below:

Column 2, line 38, Change "C$\alpha$CH$_3$" to --C$^\alpha$CH$_3$--,
Column 2, line 39, Change "C$\alpha$CH$_3$" to --C$^\alpha$CH$_3$--.
Column 5, line 38, Change "HCI" to --HCl--.
Column 11, line 35, Change "lll" to --III--.
Column 14, line 10, Insert a hyphen in "stress-induced",
Column 14, line 24, After "Orn," delete --and--,
Column 14, line 33, Change "C$\alpha$CH$_3$" to --C$^\alpha$CH$_3$--,
Column 14, line 34, Change "C$\alpha$CH$_3$" to --C$^\alpha$CH$_3$--,
Column 14, line 50, Correct the spelling of "benzoyl".
Column 15, line 13, Insert a comma before "R$_{27}$",
Column 15, line 16, Before "are" insert --R$_{41}$--.
Column 16, line 20, Correct the spelling of "hydrogen".

Signed and Sealed this

Sixth Day of January, 1987

Attest:

DONALD J. QUIGG

Attesting Officer     Commissioner of Patents and Trademarks